United States Patent [19]

Akiyama et al.

[11] Patent Number: 5,304,550
[45] Date of Patent: Apr. 19, 1994

[54] DRUG EFFECT-ENHANCING AGENT FOR ANTITUMOR DRUG

[75] Inventors: Shin-ichi Akiyama, Kagoshima; Ryozo Sakoda; Kiyotomo Seto, both of Funabashi; Norimasa Shudo, Shiraoka, all of Japan

[73] Assignee: Nissan Chemical Industries Ltd., Tokyo, Japan

[21] Appl. No.: 57,902

[22] Filed: May 7, 1993

Related U.S. Application Data

[60] Division of Ser. No. 865,489, Apr. 9, 1992, which is a division of Ser. No. 729,904, Jul. 15, 1991, Pat. No. 5,130,303, which is a continuation of Ser. No. 386,254, Jul. 28, 1989, abandoned.

[30] Foreign Application Priority Data

Aug. 2, 1988 [JP] Japan ............................. 63-193002
Jun. 30, 1989 [JP] Japan ............................. 1-168549

[51] Int. Cl.$^5$ .............. A61K 31/44; A61K 31/55; A61K 31/535; A61K 31/675
[52] U.S. Cl. ........................ 514/85; 514/89; 514/90
[58] Field of Search ................ 514/85, 89, 90

[56] References Cited

PUBLICATIONS

Kamiwatari, Mikio, Chemical Abstract 113:34417h (1990); from Kagoshima Daigaku Igaku Zasshi 41(3), (1989), pp. 225–234.

*Primary Examiner*—Mukund J. Shah
*Assistant Examiner*—Philip I. Datlow
*Attorney, Agent, or Firm*—Oblon, Spivak, McClelland, Maier & Neustadt

[57] ABSTRACT

Compounds of the formula (I):

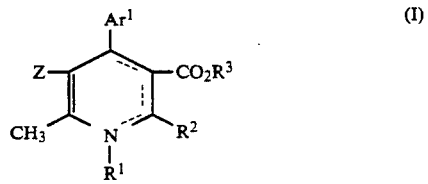

in which the nitrogen-containing hetero ring portion is 1,4-dihydropyridine ring or a pyridine ring, $R^1$ is only present when the nitrogen-containing hetero ring is a 1,4-dihydropyridine ring, and Z is a group of the formula (II):

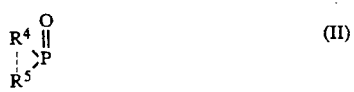

in which $R^4$ and $R^5$ may be the same or different and together may form one divalent group, are effective agents for enhancing the antitumor effect of antitumor drugs.

2 Claims, No Drawings

DRUG EFFECT-ENHANCING AGENT FOR ANTITUMOR DRUG

This is a division, of application Ser. No. 07/865,489, filed on Apr. 9, 1992, pending which is a division of application Ser. No. 07/729,904, filed on Jul. 15, 1991, now U.S. Pat. No. 5,130,303, which as a continuation of application Ser. No. 07/386,254, filed on Jul. 28, 1989, now abandoned.

The present invention relates to an agent for enhancing the drug effects of an antitumor drug, which comprises a pyridine derivative or a pharmaceutically acceptable salt thereof, as an active ingredient.

Remarkable developments have been observed in the chemotherapy of cancer. There have been an increasing number of cases in which some of cancers have been reportedly completely healed. However, there are still a number of problems yet to be solved. Among them, to reduce the side effects, to overcome drug resistance against antitumor drugs and to prevent relapse and metastatis are problems which are desired to be solved as soon as possible. Further, no antitumor drugs have been developed which are truly effective against solid cancers such as carcinoma of the colon, cancer of the stomach and carcinoma of the esophagus.

In the clinical field, it is frequently experienced that antitumor drugs which were initially effective, tend to be non effective during an extended period of treatment. Further, when a tumor metastasizes or recurs, an antitumor agent is no longer effective in many cases.

Among various factors attributable to such tendency, it is known to be an important factor that cancer cells acquire drug resistance against antitumor drugs.

Yet, it frequently happens that cancer cells which acquired drug resistance against a certain particular antitumor drug, also show resistance against many other antitumor drugs which are totally different from the particular antitumor drug in their chemical structures or functional mechanisms (multidrug resistance), which constitutes a serious obstacle in the chemotherapy of cancer.

The study on the multidrug resistance against antitumor drugs has been rapidly progressed in recent years, and a part of the mechanism has been made clear. Namely, in the cancer cells which acquire resistance, an increase of a certain P-glycoprotein is observed which has a function of a drug efflux pump, whereby the antitumor drug is pumped out of the cells in an energy dependent fashion, and consequently, the concentration of the antitumor agent in the cells decreases.

Tsuruo et al have found that Verapamil i.e. one of calcium antagonistic drugs overcomes the multidrug resistance against antitumor drugs (see Cancer Res. 41; 1967–1972 (1981)).

Akasawa et al have reported that calcium antagonistic drug nicardipin enhances the antitumor activities of vindecine sulfate (Cancer and Chemotherapy, vol. 11, 943–947 (1984)). It has also been reported that calcium antagonistic drug diltiazem enhances the drug effects of vincristine (VCR) (see Japanese Unexamined Patent Publication No. 208222/1983).

These three drugs are all calcium antagonistic substances, but they have no structural similarity at all. Further, it is known that there is no relationship between the strength of the calcium antagonistic effects and the strength of the effects for enhancing the drug effects of the antitumor drugs.

Further, certain dihydropyridine compounds are known to increase the sensitivity of cancer cells to carcinostatic drugs (see Japanese Unexamined Patent Publication No. 135381/1988) or to be effective for preventing metastatis of cancer (Japanese Unexamined Patent Publication No. 87516/1987).

It has already been known that 1,4-dihydropyridines among the compounds of the present invention have strong vasodilator activities by calcium antagonism, and they are useful as pharmaceuticals effective against hypertension, angina pectoris or disorder of cerebral circulation (U.S. Pat. Nos. 3,485,847, 3,644,627, 3,985,758 and 4,576,934).

On the other hand, substantially nothing has been known with respect to the biological activities of the pyridines of the present invention.

The present inventors have found surprisingly that the compounds of the formula I as defined hereinafter and their pharmaceutically acceptable salts are effective not only to suppress or diminish the drug resistance against cancer cells which acquired the drug resistance against antitumor drugs, but also to enhance the drug effects of antitumor drugs against cancer cells having no resistance. The present invention has been accomplished on the basis of this discovery.

The present invention provides an agent for enhancing the drug effects of an antitumor drug, which comprises a compound of the formula I:

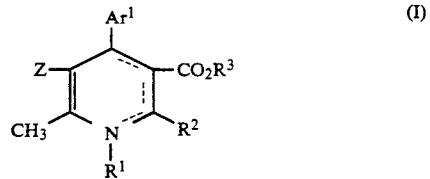

wherein
Ar$^1$ is phenyl, pyridyl, furyl or 2,1,3-benzooxadiazol-4-yl, which may be substituted by one or two substituents selected from the group consisting of NO$_2$, CF$_3$, Br, Cl, F, R$^6$ (wherein R$^6$ is C$_1$–C$_4$ alkyl), OH, OR$^6$, OCHF$_2$, COOR$^6$, NH$_2$, NHR$^6$, NR$^6$R$^7$ (wherein R$^7$ has the same meaning as R$^6$), CONH$_2$, CONHR$^6$, CONR$^6$R$^7$, COSR$^6$, SR$^6$, S(O)R$^6$, S(O)$_2$R$^6$, SO$_3$H, SO$_3$R$^6$, SO$_2$NH$_2$, SO$_2$NHR$^6$, SO$_2$NR$^6$R$^7$, CN and phenyloxy;
the nitrogen-containing hetero ring portion represents a 1,4-dihydropyridine ring or a pyridine ring;
Z is a group of the formula II:

wherein each of R$^4$ and R$^5$ which may be the same or different is OH, C$_1$–C$_{12}$ linear or branched primary or secondary alkyloxy, C$_3$–C$_6$ linear or branched unsaturated alkyloxy, C$_3$–C$_6$ cycloalkyloxy, C$_1$–C$_6$ alkoxy substituted by C$_3$–C$_6$ cycloalkyl, OAr$^2$ (wherein Ar$^2$ is phenyl which may be substituted by halogen, C$_1$–C$_3$ alkyl or C$_1$–C$_3$ alkoxy), OANR$^6$R$^7$ (wherein A is C$_2$–C$_6$ alkylene which may be substituted by C$_1$–C$_3$ alkyl or Ar$^2$), OAN(CH$_2$Ar$^2$)R$^6$, OAOR$^6$, OACN, NH$_2$, NHR$^6$, NR$^6$R$^7$, 1-piperidinyl or 1-pyrrolidinyl, or R$^4$ and R$^5$ together form OYO (wherein Y is C$_2$–C$_4$ linear saturated or unsaturated alkylene which may be substituted by $R^6$, $CO_2R^6$, $OR^6$ or A), NHYO, $R^6$NYO, NHYNH, $R^6$NYNH or $R^6$NYN$R^7$, or Z is $CO_2R^8$ (wherein $R^8$ has the same meaning as $R^3$ defined hereinafter);

$R^1$ is present only when the nitrogen-containing hetero ring is a 1,4-dihydropyridine ring, and it is hydrogen $R^6$, AN$R^6R^7$, AN(CH$_2$CH$_2$)$_2$O, AO$R^6$ or CH$_2$phenyl;

$R^2$ is $R^6$, $Ar^2$, $Ar^2$CH=CH, $Ar^2$CH(OH)CH$_2$, CHO, CN, CH$_2$OH, CH$_2$O$R^6$, CH$_2$CH$_2$N(CH$_2$CH$_2$)$_2$N$R^6$, NH$_2$, NH$R^6$ or N$R^6R^7$;

$R^3$ is hydrogen, $C_1$–$C_{12}$ linear or branched alkyl, $C_3$–$C_6$ linear or branched unsaturated alkyl, $C_3$–$C_6$ cycloalkyl, $C_1$–$C_6$ alkyl substituted by $C_3$–$C_6$ cycloalykl, AO$R^6$, AO(CH$_2$)$_m$Ar$^2$ (wherein m is an integer of from 0 to 3), (CH$_2$)$_m$Ar$^2$, ANH$_2$, ANH$R^6$, AN$R^6R^7$, AN$R^6$(CH$_2$)$_m$Ar$^2$, AN{(CH$_2$)$_m$Ar$^2$}{(CH$_2$)$_n$Ar$^3$} (wherein n has the same meaning as m, and Ar$^3$ has the same meaning as Ar$^2$), 1-benzyl-4-piperidinyl, 1-benzyl-2-piperidinyl, 2-pyridinylmethyl, 3-pyridinylmethyl, AQ (wherein Q is pyrrolidine or piperidine which may be substituted by (CH$_2$)$_m$Ar$^2$), 4-$R^6$-1-piperazinyl, 4-Ar$^2$-1-piperazinyl, 4-(Ar$^2$)$_2$CH-1piperazinyl or 4-(Ar$^2$)$_2$CH-1-(1,4-diazacycloheptyl);

or a pharmaceutically acceptable salt of the compound.

In this specification, "the compound of the present invention" refers generally to not only the compound of the formula I but also to the pharmaceutically acceptable salt thereof.

Now, the various substituents in the formula I for the compound of the present invention will be described specifically.

$R^1$ includes, for example, methyl, ethyl, methoxymethyl, methoxyethyl, aminoethyl, dimethylaminoethyl and benzyl.

$R^2$ includes, for example, methyl, phenyl, styryl, cyano, amino, methylamino, dimethylamino and hydroxymethyl.

$R^3$ includes, for exmaple, hydrogen, methyl, ethyl, n- and i-propyl, n-, i- and sec-butyl, n-pentyl, n-hexyl, n-octyl, n-decyl, cyclopropyl, cyclopentyl, cyclohexyl, cyclopropylmethyl, cyclopropylethyl, cyclohexylmethyl, cyclohexylethyl, allyl, 1-methylallyl, 2-methylallyl, 3-methylallyl, 2-propynyl, 3-butynyl, phenyl, p-chlorophenyl, p-methoxyphenyl, benzyl, p-chlorobenzyl, p-methoxybenzyl, phenethyl, p-chlorophenethyl, p-methoxyphenethyl, methoxyethyl, ethoxyethyl, i-propoxyethyl, dimethylaminoethyl, benzylmethylaminopropyl, benzyloxyethyl, n-propoxyethyl, cyanoethyl, methylaminoethyl, aminoethyl, benzylmethylaminoethyl, benzylphenylaminoethyl, 1-benzylpyridino-4-yl, 1-benzylpiperidino-2-yl, 2-pyridinomethyl, 4-diphenylmethyl-1-piperadinoethyl, 4-methyl-1-piperadinoethyl, 4-phenyl-1-piperadinoethyl, 2-oxopropyl and methylthioethyl.

Each of $R^4$ and $R^5$ includes, for example, hydroxy, methoxy, ethoxy, n- and i-propoxy, n-, i- and sec-butoxy, n-pentyloxy, n-hexyloxy, n-octyloxy, n-decyloxy, cyclopropyloxy, cyclopentyloxy, cyclohexyloxy, cyclopropylmethyloxy, cyclopropylethyloxy, cyclohexylmethyloxy, cyclohexylethyloxy, allyloxy, 1-methylallyloxy, 2-methylallyloxy, 3-methylallyloxy, 2-propynoxy, 3-butynoxy, phenyloxy, p-chlorophenyloxy, p-methoxyphenyloxy, benzyloxy, p-chlorobenzyloxy, p-methoxybenzyloxy, phenethyloxy, p-chlorophenethyloxy, p-methoxyphenethyloxy, methoxyethyloxy, ethoxyethyloxy, i-propoxyethyloxy, dimethylaminoethyloxy, benzylmethylaminopropyloxy, benzyloxyethyloxy, n-propoxyethyloxy, cyanoethyloxy, amino, methylamino, dimethylamino, diisopropylamino, 1-piperidinyl and 1-pyrrolidinyl.

The case where $R^4$ and $R^5$ together form a ring includes, for example, 1,2-dimethylethylenedioxy, 1,3-propylenedioxy, 2,2-dimethyl-1,3-propylenedioxy, 1,3-dimethyl-1,3-propylenedioxy, 2,2-diethyl-1,3-propylenedioxy, 2-ethyl-1,3-propylenedioxy, 2-isopropyl-1,3-propylenedioxy, 2-cyclobutyl-1,3-propylenedioxy, 2-cyclohexyl-1,3-propylenedioxy, 2,2-diethoxy-1,3-propylenedioxy, 1,1,3,3-tetramethyl-1,3-propylenedioxy, 1,4-dimethyl-1,4-butylenedioxy, 2-dihydro-1,4-butylenedioxy, N-methyl-1,3-dimethylpropyleneaminooxy, N-methyl-1-methylethyleneaminooxy, N,N'-methylethylenediamino and N,N'-diethylethylenediamino.

Ar$^1$ includes, for example, phenyl, nitrophenyl, chlorophenyl, fluorophenyl, trifluoromethylphenyl, hydroxyphenyl, methoxyphenyl, methoxycarbonylphenyl, aminophenyl, methylaminophenyl, dimethylaminophenyl, aminocarbonylphenyl, methylaminocarbonylphenyl, dimethylaminocarbonylphenyl, methylphenyl, methylthiocarbonylphenyl, methylthiophenyl, methylsulfonylphenyl, sulfonylphenyl, methoxysulfonylphenyl, aminosulfonylphenyl, methylaminosulfonylphenyl, dimethylaminosulfonylphenyl and o-, m- and p-substituted cyanophenyl, 2,3-dichlorophenyl and 2,1,3-benzooxadiazol-4-yl.

Among the compounds of the present invention, those of the formula I wherein either one of substituents $R^1$, $R^2$, $R^3$, $R^4$ and $R^5$ contains at least one basic nitrogen atom capable of forming a salt, or pharmaceutically acceptable salts thereof are preferred, since they present preferred drug effect-enhancing agents for antitumor drugs.

Among the compounds of the present invention, those wherein the nitrogen-containing hetero ring is a 1,4-dihydropyridine ring, are covered by the following Japanese Unexamined Patent Publications and can be prepared in accordance with the method disclosed in these publications.

Japanese Unexamined Patent Publications No. 161392/1984, No. 69089/1985, No. 248693/1985, No. 258194/1985, No. 27995/1986, No. 30591/1986, No. 37793/1986,.No. 63688/1986, No. 63689/1986, No. 210092/1986, No. 254596/1986, No. 257995/1986, No. 169795/1987, No. 195392/1987, No. 68591/1988, No. 115889/1988,No. 115890/1988 and No. 115891/1988.

Among the compounds of the present invention, those wherein the nitrogen-containing hetero ring is a pyridine ring, include new compounds. However, such compounds may readily be obtained by treating the corresponding 1,4-dihydropyridine derivatives with an oxidizing agent such as nitric acid, nitrous acid or chromic acid.

As described hereinafter, the compounds of the present invention enhance the drug effects of antitumor drugs not only against cancer cells which acquired drug resistance but also against cancer cells having no drug resistance. Therefore, they provide excellent advantages such that the dose of antitumor drugs to patients can be reduced, and toxicity or side effects can be reduced. Further, cross resistance can be overcome, which provides an important advantage that the number of useful antitumor drugs increases so that antitumor drugs can be selected to meet the symptoms and conditions of the patients. Recurrence of cancer is one of serious problems in the clinical field of chemotherapy of cancer. In many cases, this is regarded as a state where slightly remained drug resistant tumor cells have again proliferated.

The compounds of the present invention are capable of diminishing drug resistance when used in combination with antitumor agents, and they thus can be used to prevent recurrence by killing all the tumor cells and completely healing the tumor. Further, the compounds of the present invention may be employed to prevent metastatis. The enhancement of the drug effects of antitumor drugs by the combined use of the compounds of the present invention and the antitumor agents is expected also against solid cancer such as lung cancer, liver cancer or carcinoma of the colon to which the conventional antitumor agents used to be hardly effective due to formation of multidrug resistant gene (see Fojo et al, Cancer Res., 45,3002–3007 (1986)).

The compounds of the present invention can be administered orally (in the form of tablets, pills, powders, capsules, granules, etc.) or parenteral (in the form of injection drugs, intravenous drip infusion drugs, suppositories, etc.). Further, compounds of the present invention may be administered alone or in admixture with antitumor drugs.

The dose of the compound of the present invention varies depending upon the manner of administration, the age of the patient, the type of disease, the diseased condition and the type of concurrently used antitumor agents. However, the dose is usually from 0.01 to 3 g, preferably from 0.05 to 1 g, per day for an adult. There is no particular restriction as to the concurrently used antitumor drugs. However, vina alkaloids represented by vincristine and vinblastine, adriamycin, actinomycin-D, daunomycin and colchicine may be mentioned as preferred examples.

These antitumor agents may be administered in such a dose and in such a dosage form as usually employed clinically, and they may be administered simultaneously with the compound of the present invention, or before or after the administration of the compound of the present invention. Various formulations may be employed for the oral administration of the active component of the present invention. For example, the active component may be formulated into tablets, granules, fine particles, powders, syrups or elixirs Granules and powders may be filled in capsules to obtain unit dosage formulations, as the case requires.

Among such drug formulations for oral administration, solid drugs may contain an excipient such as silicic anhydride, metasilicic acid, magnesium aluminate, synthetic aluminum silicate, lactose, sucrose, corn starch, fine crystalline cellulose or hydroxypropyl starch, a binder such as gum arabic, gelatin, tragacanth, hydroxypropyl cellulose or polyvinyl pyrrolidone, a lubricant such as magnesium stearate, talc or silica, a disintegrator such as potato starch or calcium carboxymethyl cellulose, or a wetting agent such as polyethylene glycol, sorbitan monooleate, polyoxyethylene hardened caster oil or sodium lauryl sulfate.

Tablets may be coated in accordance with a conventional method.

Among the drugs for oral administration, liquid formulations may be in the form of aqueous or oily emulsions or syrups, or may be formulated in a dry product which is capable of being dissolved with a suitable vehicle prior to its use. Such liquid formulations may contain commonly employed additives, for example, an assisting agent for emulsification such as sorbit syrup, methyl cellulose, gelatin or hydroxyethyl cellulose, an emulsifier such as lecithin sorbitan monooleate or polyoxyethylene hardened caster oil, a nonaqueous vihicle such as a fractionated coconut oil, almond oil or peanut oil, or an antiseptic such as methyl p-hydroxybenzoate, propyl p-hydroxybenzoate or sorbic acid.

These drugs for oral administration may further contain a preservative or a stabilizer, as the case requires.

When the active component of the present invention is formulated into an injection drug, it may take a form of an oil solution, an emulsion or an aqueous solution. Such liquid formulations may contain an emulsifier, a stabilizer, etc. which are commonly employed.

Depending upon the manner of administration, these drugs may contain at least 1% by weight, preferably from 5 to 50% by weight, of the active ingredient.

Further, the active ingredient of the present invention may be formulated into a suppository by a usual method.

Now, Test Examples will be given to show the drug effect enhancing activities of the compounds of the present invention for antitumor agents.

TEST EXAMPLE 1

MTT colorimetric assay performed in a 96-well plate was used for an in vitro chemosensitivity test. The assay is dependent on the reduction of MTT by the mitochondrial dehydrogenase of viable cells to a blue formazan product which can be measured spectrophotometrically. Equal numbers of cells (2,000 for KB 3-1 and 5,000 for KB–C2) were inoculated into each well with 0.18 ml of culture medium. After overnight incubation (37° C., 5% $CO_2$), 20 $\mu$l of vincristine solution and 0.5 $\mu$l of sample solution were added and incubated for 4 days. Then, 50 $\mu$l of MTT (1.1 mg/ml PBS) was added to each well and incubated for further 4 hours. The resulting formazan was dissolved with 100 $\mu$l of DMSO after aspiration of the culture medium. Plates were placed on a plate shaker for 5 minutes and read immediately at 570 nm. $IC_{50}$ (mg/ml) with a tested sample 10 $\mu$M is given in Table 1; and $IC_{50}$ of vincristine without a sample was 5,000 ng/ml.

MTT: 3-(4,5-dimethylthiazol-2-yl)-2,5-diphenyltetrazolium bromide

MEM: minimum essential medium

The test results are shown in Table 1.

TABLE 1

| Ar¹ | Z | R¹ | R² | R³ | IC$_{50}$ |
|---|---|---|---|---|---|
| 3-NO$_2$-C$_6$H$_4$- | CO$_2$Et | H | -CH$_2$CH$_2$-N(piperazine)N-CH$_3$ | Et | 5 |
| 2-(phenoxy)pyridin-6-yl- | CO$_2$Me | H | CH$_3$ | Me | 120 |
| 3-NO$_2$-C$_6$H$_4$- | (EtO)$_2$P(=O)- | H | CH$_3$ | -CH$_2$CH$_2$CH$_2$-N(CH$_3$)(CH$_2$Ph) | 30 |
| 3-Cl-C$_6$H$_4$- | (EtO)$_2$P(=O)- | H | CH$_3$ | -CH$_2$CH$_2$CH$_2$-N(CH$_3$)(CH$_2$Ph) | 12 |
| furan-2-yl- | CO$_2$Me | H | -CH$_2$CH(OH)C$_6$H$_5$ | -CH$_2$CH$_2$CH$_2$-N(CH$_3$)(CH$_2$Ph) | 6 |
| pyridin-2-yl- | CO$_2$Me | H | -CH$_2$CH(OH)C$_6$H$_5$ | -CH$_2$CH$_2$CH$_2$-N(CH$_3$)(CH$_2$Ph) | 27 |
| 3-CF$_3$-C$_6$H$_4$- | (EtO)$_2$P(=O)- | H | CH$_3$ | -CH$_2$CH$_2$CH$_2$-N(CH$_3$)(CH$_2$Ph) | 15 |

TABLE 1-continued

| Ar¹ | Z | R¹ | R² | R³ | IC₅₀ |
|---|---|---|---|---|---|
| Ph | (EtO)₂P(=O)— | H | CH₃ | -CH₂CH(Ph)CH₃ , N(CH₂Ph)(CH₃) | <5 |
| 3-NO₂-C₆H₄ | (EtO)₂P(=O)— | H | CH₃ | -CH₂CH(Ph)CH₃ , N(CH₂Ph)(CH₃) | <5 |
| 3-NO₂-C₆H₄ | CO₂CH₃ | H | CH₃ | -CH₂CH(Ph)CH₃ , N(CH₂Ph)(CH₃) | 13 |
| 3-CF₃-C₆H₄ | (EtO)₂P(=O)— | H | CH₃ | -nPr, N(CH₂Ph)(CH₃) | 5 |
| 3-NO₂-C₆H₄ | (EtO)₂P(=O)— | H | CH₃ | -nPr, N(CH₂Ph)(CH₃) | 19 |
| 3-Cl-C₆H₄ | (iPrO)₂P(=O)— | H | CH₃ | -nPr, N(CH₂Ph)(CH₃) | 6 |
| 3-NO₂-C₆H₄ | (nBuO)(MeO)P(=O)— | H | CH₃ | -nPr, N(CH₂Ph)(CH₃) | 6 |

TABLE 1-continued

| Ar¹ | Z | R¹ | R² | R³ | IC₅₀ |
|---|---|---|---|---|---|
| 3-NO₂-phenyl | n-HexO-P(=O)-OMe | H | CH₃ | N(CH₂Ph)(CH₃)(n-Pr) | 6 |
| 2-CF₃-phenyl | PhCH₂N(CH₃)(CH₂)₆O-P(=O)-OCH₃ | H | CH₃ | CH₃ | <5 |
| 2-Cl-phenyl | CH₃O(CH₂)₂O-P(=O)-O(CH₂)₅CH₃ | H | CH₃ | N(CH₂Ph)(CH₃)(n-Pr) | 6 |
| 3-NO₂-phenyl | CH₃O(CH₂)₂O-P(=O)-O(CH₂)₅CH₃ | H | CH₃ | N(CH₂Ph)(CH₃)(n-Pr) | <5 |
| 3-NO₂-phenyl | (EtO)₂P(=O) | H | CH₃ | 4-(NCHPh₂)-1-(n-Pr)-piperidine | 7 |
| 3-NO₂-phenyl | CO₂CH₃ | H | CH₃ | 4-(NCHPh₂)-1-(n-Pr)-piperidine | 14 |
| 2-CF₃-phenyl | CH₃(CH₂)₅O-P(=O)-OCH₂CH₂N(CH₃)(CH₂Ph) | H | CH₃ | CH₃ | 7 |

TABLE 1-continued

| Ar¹ | Z | R¹ | R² | R³ | IC₅₀ |
|---|---|---|---|---|---|
| 2-Cl-phenyl | 4-methyl-1,3,2-dioxaphosphorinane 2-oxide | H | CH₃ | N(CH₂Ph)(propyl), CH₃ | 60 |
| 2-CF₃-phenyl | P(=O)(OEt)(NEt₂) | H | CH₃ | N(CH₂Ph)(propyl), CH₃ | 10 |
| 3-Cl-phenyl | P(=O)(NEt₂)₂ | H | CH₃ | N(CH₂Ph)(propyl), CH₃ | 21 |
| 3-NO₂-phenyl | P(=O)(NEt₂)₂ | H | CH₃ | N(CH₂Ph)(propyl), CH₃ | <10 |
| 3-Cl-phenyl | 1,3-dimethyl-1,3,2-diazaphospholidine 2-oxide | H | CH₃ | N(CH₂Ph)(propyl), CH₃ | 320 |
| 3-NO₂-phenyl | 1,3-dimethyl-1,3,2-diazaphosphorinane 2-oxide | H | CH₃ | N(CH₂Ph)(propyl), CH₃ | 300 |

TABLE 1-continued

| Ar¹ | Z | R¹ | R² | R³ | IC₅₀ |
|---|---|---|---|---|---|
| 3-NO₂-phenyl | N,N'-dimethyl-1,3,2-diazaphospholidine 2-oxide | H | CH₃ | N(CH₂Ph)(CH₃)(n-Pr) | 68 |
| 3-CF₃-phenyl | (EtO)₂P(O) | — | CH₃ | N(CH₂Ph)(CH₃)(n-Pr) | <5 |
| 2,3-diCl-phenyl | N,N'-dimethyl-1,3,2-diazaphospholidine 2-oxide | H | CH₃ | N(CH₂Ph)(CH₃)(n-Pr) | 250 |
| 2-Cl-phenyl | N,N'-dimethyl-1,3,2-diazaphospholidine 2-oxide | H | CH₃ | N(CH₂Ph)(CH₃)(n-Pr) | 32 |
| 3-Cl-phenyl | N,N'-dimethyl-1,3,2-diazaphospholidine 2-oxide | H | CH₃ | 4-(N=CHPh₂)-1-(n-Pr)-piperazine | 660 |

TABLE 1-continued
| Ar¹ | Z | R¹ | R² | R³ | IC₅₀ |
|---|---|---|---|---|---|
| 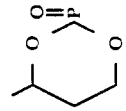 | 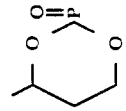 | — | CH₃ | 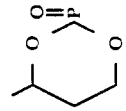 | 52 |
| 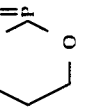 |  | H | CH₃ | 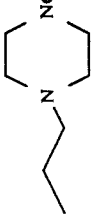 | 32 |
| 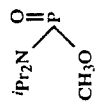 |  | H | CH₃ | 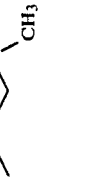 | 210 |
| 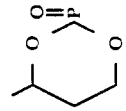 | 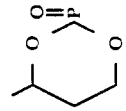 | — | CH₃ | 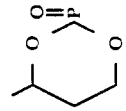 | 42 |
| 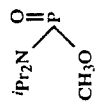 |  | H | CH₃ | Me | 520 |
|  | 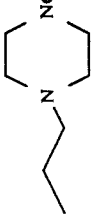 | H | CH₃ | 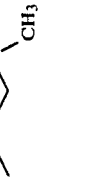 | 25 |

TABLE 1-continued
| Ar¹ | Z | R¹ | R² | R³ | IC₅₀ |
|---|---|---|---|---|---|
| 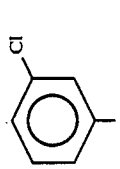 |  | H | CH₃ | 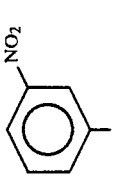 | <10 |
|  | 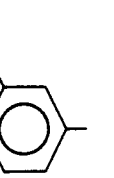 | H | CH₃ |  | <5 |
| 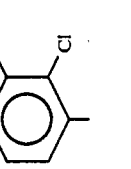 |  | H | CH₃ | 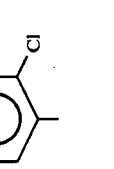 | <10 |
| 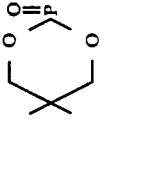 | 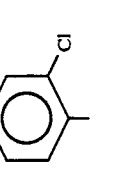 | H | CH₃ |  | <5 |
| 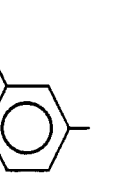 |  | H | CH₃ | | 52 |
| | | H | CH₃ | | 260 |
| | | H | CH₃ | | 5 |

TABLE 1-continued

| $Ar^1$ | Z | $R^1$ | $R^2$ | $R^3$ | $IC_{50}$ |
|---|---|---|---|---|---|
| 2-methyl-3-chlorophenyl | bicyclic phosphate | H | $CH_3$ | $(CH_2)_6N(Ph)(CH_3)CH_2Ph$ — actually $(CH_2)_6N(CH_3)CH_2Ph$ | 5 |
| 2-methyl-3-nitrophenyl | bicyclic phosphate | H | $CH_3$ | $(CH_2)_6N(CH_3)CH_2Ph$ | <5 |
| 2-methyl-3-chlorophenyl | bicyclic phosphate | H | $CH_3$ | N-benzyl-2-methylpiperidine | 100 |
| 2-methyl-3-nitrophenyl | bicyclic phosphate | H | $CH_3$ | N-benzyl-2-methylpiperidine | <5 |
| 3-nitro-methylphenyl | bicyclic phosphate | H | $CH_3$ | cinnamyl | 500 |
| 3-nitro-methylphenyl | bicyclic phosphate | H | $CH_3$ | 4-(N-diphenylmethylamino)-1-propylpiperidine | <5 |
| 3-nitro-methylphenyl | bicyclic phosphate | H | $CH_3$ | 1-(3-phenylpropyl)-4-propylpiperazine | 200 |

TABLE 1-continued
| Ar¹ | Z | R¹ | R² | R³ | IC₅₀ |
|---|---|---|---|---|---|
|  | 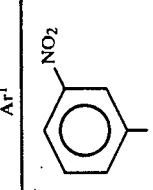 | H | CH₃ | 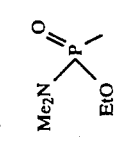 | 260 |
| 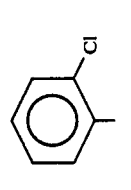 | 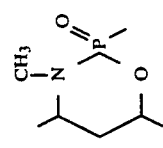 | H | CH₃ | 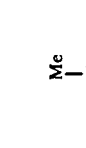 | 35 |
| 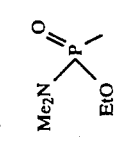 | 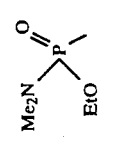 | H | CH₃ | 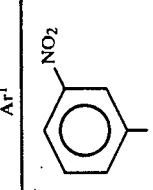 | 410 |
| 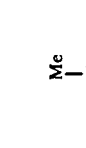 | 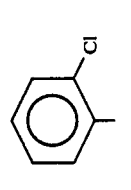 | H | CH₃ | 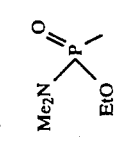 | 560 |
| 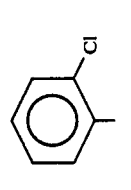 | 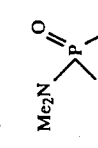 | H | CH₃ | 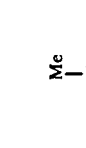 | 300 |
| 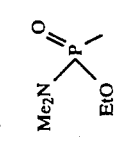 |  | H | CH₃ | 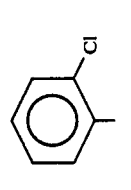 | <10 |
| 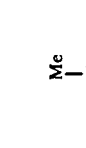 | 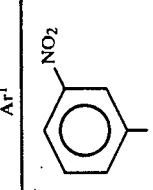 | H | CH₃ | 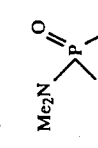 | 120 |

TABLE 1-continued

| Ar¹ | Z | R¹ | R² | R³ | IC₅₀ |
|---|---|---|---|---|---|
| 3-CF₃-phenyl | O=P(OCH₂C(CH₃)₂CH₂O) cyclic | H | CH₃ | 1-propyl-4-(NCHPh₂)piperidine | 9 |
| 3-CF₃-phenyl | O=P(OCH₂C(CH₃)₂CH₂O) cyclic | H | CH₃ | N(CH₂Ph)(CH₃)(propyl) | 41 |
| 3-NO₂-phenyl | O=P(OCH(CH₃)CH₂CH(CH₃)O) cyclic | I | CH₃ | 1-propyl-4-(NCHPh₂)piperidine | <5 |
| 3-NO₂-phenyl | O=P(OCH₂C(CH₃)₂CH₂O) cyclic | H | CH₃ | 1-propyl-4-[NCH(4-F-phenyl)₂]piperidine | 500 |
| 2-OCHF₂-phenyl | O=P(OCH₂C(CH₃)₂CH₂O) cyclic | H | CH₃ | N(CH₂Ph)(Ph)(propyl) | 9 |
| 2-OCHF₂-phenyl | O=P(OCH₂C(CH₃)₂CH₂O) cyclic | H | CH₃ | 1-propyl-4-(NCHPh₂)piperidine | 6 |
| 4-benzofurazanyl | O=P(OCH₂C(CH₃)₂CH₂O) cyclic | H | CH₃ | 1-propyl-4-(NCHPh₂)piperidine | 50 |

TABLE 1-continued

| Ar¹ | Z | R¹ | R² | R³ | IC₅₀ |
|---|---|---|---|---|---|
| benzofurazan-4-yl | P(=O)(OCH₂)₂C(CH₃)₂ | H | CH₃ | CH₂N(Ph)(CH₃)(propyl) | 900 |
| 2,3-dichlorophenyl | P(=O)(OCH(CH₃))₂CH₂ (trans-dimethyl) | H | CH₃ | 4-Ph-1-propylpiperidinyl | 6 |
| 3-nitrophenyl | P(=O)(OCH(CH₃))₂CH₂ (cis-dimethyl) | H | CH₃ | 4-Ph-1-propylpiperidinyl | <5 |
| 3-CF₃-phenyl | P(=O)(OCH₂)₂C(CH₃)₂ | H | CH₃ | NCH(4-F-C₆H₄)₂ with 4-propylpiperazinyl | 8 |
| 3-nitrophenyl | P(=O)(OCH₂)₂C(CH₃)₂ | H | CH₃ | CH₂N(Ph)(Ph)(propyl) | 200 |
| 3-nitrophenyl | P(=O)(OCH₂)₂C(CH₃)₂ | H | CH₃ | CH₂N(CH₂Ph)(CH₃)(neopentyl) | 220 |
| 3-nitrophenyl | CO₂Me | H | CH₃ | CH=CH-Ph | 38 |

TABLE 1-continued

| Ar¹ | Z | R¹ | R² | R³ | IC₅₀ |
|---|---|---|---|---|---|
| 3-NO₂-C₆H₄ | 5,5-dimethyl-1,3,2-dioxaphosphorinan-2-yl 2-oxide | H | CH₃ | N(CH₂Ph)(CH₃) on 2-methylcyclohexyl | 130 |
| 3-NO₂-C₆H₄ | 5,5-dimethyl-1,3,2-dioxaphosphorinan-2-yl 2-oxide | H | CH₃ | N(CH₃)(CHPh₂)propyl | 500 |
| 2-Cl-C₆H₄ | 5,5-dimethyl-1,3,2-dioxaphosphorinan-2-yl 2-oxide | H | CH₃ | N(CH₃)(CHPh₂)propyl | 12 |
| 3-NO₂-C₆H₄ | 5,5-dimethyl-1,3,2-dioxaphosphorinan-2-yl 2-oxide | H | CH₃ | 4-(NCHPh₂)piperidin-1-yl propyl | 5 |
| 3-NO₂-C₆H₄ | 5,5-dimethyl-1,3,2-dioxaphosphorinan-2-yl 2-oxide | H | CH₃ | N(CH₂Ph)₂ butyl | 190 |
| 3-NO₂-C₆H₄ | 5,5-dimethyl-1,3,2-dioxaphosphorinan-2-yl 2-oxide | H | CH₃ | 4-(NCHPh₂)piperidin-1-yl propyl | 5 |
| 3-NO₂-C₆H₄ | 5,5-dimethyl-1,3,2-dioxaphosphorinan-2-yl 2-oxide | H | CH₃ | N(Ph)₂ propyl | 280 |

TABLE 1-continued

| Ar¹ | Z | R¹ | R² | R³ | IC₅₀ |
|---|---|---|---|---|---|
| 3-NO₂-phenyl | bicyclic phosphate (neopentyl) | H | CH₃ | piperazine-N-butyl, N'-CH=N-bis(4-F-phenyl) | 6 |
| 3-NO₂-phenyl | bicyclic phosphate (neopentyl) | H | CH₃ | N(CH₂Ph)(Ph)(CH₂CH(CH₃)₂) | 13 |
| 3-NO₂-phenyl | bicyclic phosphate (neopentyl) | H | CH₃ | 4-Ph-piperidine, N-butyl | 10 |
| 3-NO₂-phenyl | dioxaphosphorinane (gem-dimethyl) | H | CH₃ | N(CH₂Ph)(CH₃)(CH₂CH₂CH₂-) with Ph | 170 |
| 3-NO₂-phenyl | dioxaphosphorinane (gem-dimethyl) | H | CH₃ | N(CH₂Ph)(Ph)(propyl) | 20 |
| 3-NO₂-phenyl | P-methyl dioxaphosphorinane | H | CH₃ | 4-Ph-piperidine, N-propyl | 6 |
| 3-NO₂-phenyl | dioxaphosphorinane (gem-dimethyl) | H | CH₃ | N(CH₂Ph)(Ph)(CH₂CH(CH₃)₂) | 200 |

TABLE 1-continued

| Ar¹ | Z | R¹ | R² | R³ | IC₅₀ |
|---|---|---|---|---|---|
| 4-methylbenzo[1,2,5]oxadiazole | 5,5-dimethyl-2-oxo-1,3,2-dioxaphosphinane | H | CH₃ | 1-propyl-4-(N-benzhydryl)piperazine | 40 |
| 4-methylbenzo[1,2,5]oxadiazole | 5,5-dimethyl-2-oxo-1,3,2-dioxaphosphinane | H | CH₃ | N-benzyl-N-phenyl-propylamine | 28 |
| 3-nitrophenyl | 5,5-dimethyl-2-oxo-1,3,2-dioxaphosphinane | H | CH₃ | 1-propyladamantane | 35 |
| 3-nitrophenyl | 5,5-diethyl-2-oxo-1,3,2-dioxaphosphinane | H | CH₃ | 1-propyl-4-(N-benzhydryl)piperazine | 6 |
| 3-nitrophenyl | 5-isopropyl-2-oxo-1,3,2-dioxaphosphinane | H | CH₃ | 1-propyl-4-(N-benzhydryl)piperazine | 7 |
| 3-nitrophenyl | 5,5-dimethyl-2-oxo-1,3,2-dioxaphosphinane | CH₂CH₂-morpholino | CH₃ | N-benzyl-N-phenyl-propylamine | <5 |
| 3-nitrophenyl | 5,5-dimethyl-2-oxo-1,3,2-dioxaphosphinane | H | CH₃ | farnesyl | 28 |

TABLE 1-continued

| Ar¹ | Z | R¹ | R² | R³ | IC₅₀ |
|---|---|---|---|---|---|
| 3-NO₂-C₆H₄ | phosphorinane | H | CH₃ | 2-propylindene | 5 |
| 3-NO₂-C₆H₄ | phosphorinane | — | CH₃ | PhNH-CH(propyl) | <10 |
| 3-NO₂-C₆H₄ | phosphorinane | H | CH₃ | PhCH₂CH₂N(Ph)(propyl) | 8 |
| 3-NO₂-C₆H₄ | phosphorinane | H | CH₃ | PhCH=CH-N(Ph)(propyl) | 500 |
| 3-NO₂-C₆H₄ | phosphorinane | H | CH₃ | 4-(PhCH₂O)C₆H₄CH₂- | 8 |
| 3-NO₂-C₆H₄ | phosphorinane | — | CH₃ | PhCH₂N(Ph)(propyl) | 540 |
| 3-NO₂-C₆H₄ | CO₂Me | — | CH₃ | 4-(Ph₂CHN)-piperazinyl-propyl | 54 |

TABLE 1-continued

| Ar¹ | Z | R¹ | R² | R³ | IC₅₀ |
|---|---|---|---|---|---|
| 3-NO₂-C₆H₄ | CO₂Me | — | CH₃ | N(CH₂Ph)(CH₃)(n-Pr) | 14 |
| 3-CF₃-C₆H₄ | cyclic phosphonate (5,5-diethyl-2-oxo-1,3,2-dioxaphosphorinane) | — | CH₃ | 4-(NCHPh₂)-1-(n-Pr)-piperidine | 6 |
| 3-NO₂-C₆H₄ | CO₂Me | — | CH₃ | CH=CH-CH₂-Ph | 67 |

TEST EXAMPLE 2

300 human carcinoma KB-3-1 cells or multidrug resistant KB-Cl cells were incubated in a glucose culture medium for 16 hours. A solution of vincristine alone, or of vincristine and a sample compound in DMSO, was added thereto, and the cells were incubated at 37° C. for further 10 days. Colonies were stained with a 0.5% methylene blue in 50% ethanol, and counted. The concentration of vincristine inhibiting the formation of the cell colonies 50% ($IC_{50}$) was investigated in the presence or absence of the sample. Each value represents relative resistance to vincristine that was determined by dividing the $IC_{50}$ of KB-3-1 for vincristine in the presence of a sample or the $IC_{50}$ of KB-Cl for vincristine in the absence of the sample by the $IC_{50}$ of KB-3-1 for vincristine in the absence of the sample.

The test results are shown in Table 2.

The analytical values are shown below.

NMR δ(ppm) $CDCl_3$: 1.02(3H,dd,J=1.6Hz,6.2Hz), 1.16(3H,dd,J=1.6Hz,6.2Hz 1.12(1H,m), 1.57(1H ,m), 2.20–2.50(10H,m), 2.59(3H,s), 2.99(3H,s), 3.90–4.10(2H,m), 4.19(1H ,s), 4.60–4.80(2H,m), 7.17(2H,t,J=7.4Hz), 7.26(4H,dd,J=7.4Hz,7.0Hz), 7.39(4H,d,J=7.0Hz), 7.53(1H ,m), 7.59(1H ,m), 8.15(1H ,m), 8.25(1H ,m)

MS(FAB) 699 (50%, M+1), 167 (100%)

OXIDATION EXAMPLE 2

Preparation of 5-(5,5-dimethyl-1,3,2-dioxaphosphorinan-2-yl)-2,6-dimethyl-4-(3-nitrophenyl]-3-pyridinecarboxylic acid 2-(N-phenyl]aminoethylester p-oxide 5.6 g of 5-(5,5-dimethyl-1,3,2-dioxaphosphorinan 2-yl)-1,4-dihydro-2,6-dimethyl-4 (3-nitrophenyl)-3pyridinecarboxylic acid 2-(N-phenyl)aminoethylester

TABLE 2

Activities for enhancing drug effects of vincristine against parent strain (KB-3-1) and its drug resistant strain (KB-Cl)

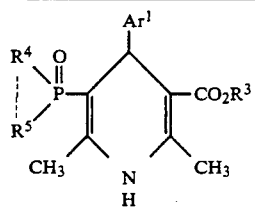

(In the Table, Ph means phenyl.)

| Compound No. | $Ar^1$ | $R^3$ | $R^4$---$R^5$ | Concentration (μg/ml) | KB-3-1 | KB-Cl |
|---|---|---|---|---|---|---|
|  | No administration |  |  | 0 | 1 | 1200 |
| (1) | m-Nitrophenyl | $CH_2CH_2N(CH_3)CH_2Ph$ | $OCH_2C(CH_3)_2CH_2O$ | 10 | 0.2 | 34 |
| (2) | m-Nitrophenyl | 2-(4-diphenylmethyl-1-piperazinyl)ethyl | $OCH(CH_3)CH_2CH(CH_3)O$ | 10 | 0.1 | 0.5 |
| (3) | m-Nitrophenyl | $CH_2CH_2N(CH_3)CH_2Ph$ | $R^4$: $CH_3O$ <br> $R^5$: $CH_3O$ | 10 | 0.2 | 14 |
| (4) | m-Nitrophenyl | $CH_3$ | $R^4$: $PhCH_2N(CH_3)(CH_2)_3O$ <br> $R^5$: $CH_3O$ | 10 | 0.1 | 18 |
| (5) | m-Nitrophenyl | $CH_2CH_2N(CH_3)CH_2Ph$ | $R^4$: $(CH_3)_2N$ <br> $R^5$: $C_2H_5O$ | 10 | 0.1 | 0.7 |
| (6) | m-Chlorophenyl | $CH_2CH_2N(CH_3)CH_2Ph$ | $N(CH_3)CH_2CH_2N(CH_3)$ | 10 | 0.1 | 1.0 |

Now, two typical methods for oxidizing, 1,4-dihydropyridine derivatives to the corresponding pyridine derivatives, will be described in detail.

OXIDATION EXAMPLE 1

Preparation of 5-(cis-4,6-dimethyl-1,3,2-dioxaphosphorinan-2-yl)-2,6-dimethyl-4-(3-nitrophenyl)-3-pyridinecarboxylic acid 4-diphenylmethyl-1-piperadionethylester p-oxide 10 ml of 36% nitric acid was added to 1.4 g of 5-(cis-4,6-dimethyl-1,3,2-dioxaphosphrinan-2-yl)-1,4-dihydro-2,6-dimethyl-4-(3-nitrophenyl)-3-pyridinecarboxylic acid 4-diphenylmethyl-1-piperadinoethylester p-oxide dihydrochloride, and the mixture was stirred at 50° C. for 10 minutes.

After cooling, the mixture was neutralized with a saturated sodium hydrogen carbonate aqueous solution and extracted with chloroform. The extract was dried over anhydrous sodium sulfate. Then, the solvent was distilled off under reduced pressure, and the residue was subjected to silica gel chromatography (developing solvent: ethyl acetate Rf=0.5) to obtain 1.2 g (yield 95%) of the above identified compound as yellow oily substance.

p-oxide was dissolved in 20 ml of acetic acid. After adding 2 g of chromium trioxide, the mixture was heated at 100° C. for 30 minutes.

After cooling, the solvent was distilled off under reduced pressure. To the residue, a saturated sodium hydorgencarbonate aqueous solution was added for neutralization, and the mixture was extracted with 100 ml of ethyl acetate. The extract was dried over anhydrous sodium sulfate, and the solvent was distilled off under reduced pressure. To the residue, 10 ml of methanol, 10 ml of ethanol and 2 g of p-toluene sulfonic acid, and the mixture was refluxed under heating for 7 hours. The solvent was distilled off under reduced pressure. Then, a saturated sodium hydrogen carbonate aqueous solution was added, and the mixture was extracted with 100 ml of ethyl acetate. The extract was dried over anhydrous sodium sulfate. Then, solvent was distilled off under reduced pressure, and the residue was subjected to silica gel chromatography (developing solvent: ethyl acetate Rf=0.6) to obtain 4.2 g of the above-identified compound (yield: 79%, melting point: 105°–106° C.) as yellow crystals.

The analytical values are shown below.

NMR δ(ppm) $CDCl_3$:

0.75(3H,s), 1.09(3H,s), 2.60(3H,s), 2.89(3H,s), 3.0–3.70(6H,m), 4.14(2H,t,J=6Hz), 6.30–8.30(9H,m)

Now, examples for the drugs containing the compounds of the present invention will be presented.

EXAMPLES 1: Hard capsules for oral administration 25 g of hydrochloride of the compound (2), 5 g of adriamycin and 7.5 g of polyoxyethylene castor oil were dissolved in methanol Then, 25 g of silicic anhydride was mixed thereto Methanol was distilled off, and then 5 g of calcium carboxymethyl cellulose, 5 g of corn starch, 7.5 g of hydroxypropyl cellulose and 20 g of fine crystal cellulose were mixed thereto. Then, 30 ml of water was added, and the mixture was kneaded and granulated. The product was granulated by a granulation machine equipped with a screen of No. 24 mesh (B.S.). Granules were dried to a water content of not higher than 5% and sieved with a screen of No. 16 mesh (B.S.). Then, the particles were filled in capsules by a capsule filling machine in an amount of 200 mg per capsule.

EXAMPLE 2

Soft capsules for oral administration 30 g of hydrochloride of compound (2), 7.5 g of adriamycin and 130 g of polyethylene glycol (Macrogol 400) were mixed to obtain a uniform solution.

Separately, a gelatin solution comprising 93 g of gelatin, 19 g of glycerol, 10 g of D sorbitol, 0.4 g of ethyl p-oxybenzoate, 0.2 g of propyl p-oxybenzoate and 0.4 g of titanium oxide, was prepared. By using this as a capsule coating agent, soft capsules each containing 190 mg of the content were prepared by a manual flat plate punching method.

EXAMPLE 3

Soft capsules for oral administration.

40 g of hydrochloride of compound (2), 4 g of adriamycin and 120 g of polyethylene glycol (Macrogol 400) were mixed to obtain a uniform solution.

Separately, a gelatin solution comprising 90 g of gelatin, 16 g of glycerol, 8 g of D sorbitol, 0.35 g of ethyl p-oxybenzoate, 0.2 g of propyl p-oxybenzoate and 0.3 g of titanium oxide, was prepared. By using this as a capsule coating agent, soft capsules each containing 180 mg of the content were prepared by a manual flat plate punching method.

EXAMPLE 4

Injection drug 1 g of hydrochloride of compound (2), 1 g of adriamycin, a suitable amount of peanut oil and 1 g of benzyl alcohol were mixed, and the total amount was brought to 100 ml by using peanut oil. The solution thus obtained was put into ampules in an amount of 1 ml under an aseptic condition and the ampules were closed.

EXAMPLE 5

Injection drug 1 g of hydrochloride of compound (2), 1 g of adriamycin, 5.0 g of hydrogenated castor oil polyoxyethylene (60 mol) ether (Nikkol HCO 60, tradename), 20 g of propylene glycol, 10 g of glycerol and 5.0 g of ethyl alcohol were mixed, and 100 ml of distilled water was added thereto. The mixture was stirred to obtain a solution. The solution was put into ampules in an amount of 2.0 ml each under an aseptic condition, and the ampules were then closed.

EXAMPLE 6

Injection drug 1 g of hydrochloride of compound (2), 1 g of adriamycin, 5.0 g of hydrogenated castor oil polyoxyethylene (60 mol) ether (Nikkol HCO 60, tradename), 20 g of propylene glycol, 10 g of glycerol and 5.0 g of ethyl alcohol were mixed, and 100 ml of distilled water was added thereto. The mixture was stirred to obtain a solution. This solution was put into ampules in an amount of 2.0 ml each under an aseptic condition, and the ampules were closed.

EXAMPLE 7

Hard capsules for oral administration.

25 g of hydrochloride of compound (2), 5 g of vincristine and 7.5 g of polyoxyethylene castor oil were dissolved in methanol. Then, 25 g of silicic anhydride was added thereto, methanol was evaporated, and 5 g of calcium carboxymethyl cellulose, 5 g of corn starch, 7.5 g of hydroxypropyl cellulose and 20 g of fine crystalline cellulose were mixed, and 30 ml of water was added thereto. The mixture was kneaded and granulated. This product was granulated by a granulator with a screen of No. 24 mesh (B.S.). Granules thus obtaines were dried to a water content of not higher 5% and then sieved with a screen with No. 16 mesh (B.S.).

Then, the particles thus obtained were filled into capsules by a capsule filling machine in an amount of 200 mg per capsule.

EXAMPLE 8

Soft capsules for oral administration 30 g of hydrochloride of compound (2), 7.5 of vincristine and 130 g of polyethylene glycol (Macrogol 400) were mixed to obtain a uniform solution.

Separately, a gelatin solution comprising 93 g of gelatin, 19 g of glycerol, 10 g of D-sorbitol, 0.4 g of ethyl p-oxybenzoate, 0.2 g of propyl p-oxybenzoate and 0.4 g of titanium oxide, was prepared. By using this as a capsule coating agent, soft capsules containing 190 mg of the content were prepared by a manual flat plate punching method.

EXAMPLE 9

Soft capsules for oral administration 40 g of hydrochloride of compound (2), 4 g of vincristine and 120 g of polyethylene glycol (Macrogol 400) were mixed to obtain a uniform solution.

Separately, a gelatin solution comprising 90 g of gelatin, 16 g of glycerol, 8 g of D-sorbitol, 0.35 g of ethyl p-oxybenzoate, 0.2 g of propyl p-oxybenzoate and 0.3 g of titanium oxide, was prepared. By using this as a capsule coating agent, soft capsules containing 180 mg of the content were prepared by a manual flat plate punching method.

EXAMPLE 10

Injection drug 1 g of hydrochloride of compound (2), 1 g of vincristine, a suitable amount of peanut oil and 1 g of benzyl alcohol were mixed, and the total amount was brought to 100 cc by using peanut oil. This solution was put into ampules in an amount of 1 ml per ampule under an aseptic condition, and the ampules were closed.

EXAMPLE 11

Injection drug 1 g of hydrochloride of compound (2), 1 g of vincristine, 5.0 g of hydrogenated castor oil polyoxyethylene (60 mol) ether (Nikkol HCO 60, tradename), 20 g of propylene glycol, 10 g of glycerol and 5.0 g of ethyl alcohol were mixed, and 100 ml of distilled water was added thereto. The mixture was stirred to obtain a solution. This solution was put into ampules in an amount of 2.0 ml per ampule under an aseptic condition, and the ampules were closed

EXAMPLE 12

Injection drug 1 g of hydrochloride of compound (2), 1 g of vincristine, 5.0 g of hydrogenated castor oil polyoxyethylene (60 mol) ether (Nikkol HCO 60, tradename), 20 g of propylene glycol, 10 g of glycerol and 5.0 g of ethyl alcohol were mixed, and 100 ml of distilled water was added thereto. The mixture was stirred to obtain a solution. This solution was put into ampules in an amount of 2.0 ml per ampule under an aseptic condition, and the ampules were closed.

Now, Examples will be given to illustrate the preparation of a drug in which the compound of the present invention is administered separately from an antitumor drug.

EXAMPLE 13

Tablets

| Composition (1,000 tablets) | |
| --- | --- |
| Hydrochloride of the compound of Example (2) | 55.0 (g) |
| Lactose | 190.0 |
| Corn starch | 75.0 |
| Fine crystalline cellulose | 25.0 |
| Methyl cellulose | 3.0 |
| Magnesium stearate | 2.0 |
| | 350.0 (g) |

The above components were charged into a V-type mixer and uniformly mixed. This powder mixture was directly tabletted to obtain tablets having a weight of 350 mg per tablet.

EXAMPLE 14

Capsules

| Composition (1,000 capsules) | |
| --- | --- |
| Hydrochloride of the compound of Example (2) | 55 (g) |
| Corn starch | 145 |
| Fine crystalline cellulose | 145 |
| Magnesium stearate | 5 |
| | 350 (g) |

The above compositions were charged into a V-type mixer and uniformly mixed. This powder mixture was filled in hard capsules The content per capsule was 350 mg.

EXAMPLE 15

Syrups

| Composition (2% solution) | |
| --- | --- |
| Hydrochloride of the compound of Example (2) | 2.0 (g) |
| Sucrose | 30.0 |
| Glycerol | 5.0 |
| Flavor | 0.1 |
| 96% Ethanol | 10.0 |
| Methyl p-oxybenzoate | 0.03 |
| Distilled water to bring the total amount to 100.0 g | |

Sucrose and hydrochloride of the compound of Example 1 were dissolved in 60 g of warm water and then cooled. Thereafter, a flavor solution dissolved in glycerol and ethanol was added thereto. Then, water was added to this mixture to bring the total amount to 100.0 g.

EXAMPLE 16

Powder

| | |
| --- | --- |
| Hydrochloride of the compound of Example (2) | 5.0 (g) |
| Lactose | 84.0 |
| Fine crystalline cellulose | 10.0 |
| Methyl cellulose | 1.0 |
| | 100.0 (g) |

The above components were charged into a V-type mixer and uniformly mixed.

EXAMPLE 17

Injection drug 1 g of hydrochloride of compound (2), a suitable amount of peanut oil and 1 g of benzyl alcohol were mixed, and the total amount was brought to 100 cc by using peanut oil. This solution was put into ampules in an amount of 1 ml per ampule under an aseptic condition, and the ampules were closed.

We claim:

1. A method for enhancing the antitumor effect of an antitumor drug, comprising administering to a patient in need thereof an effective amount of a compound of the formula I:

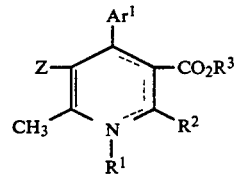

(I)

wherein $Ar^1$ is phenyl, pyridyl, furyl or 2,1,3-benzoxadiazol-4-yl, which may be substituted by one or more substitutents selected from the group consisting of $NO_2$, $CF_3$, Br, Cl, F, $R^6$ (wherein $R^6$ is $C_1$–$C_4$ alkyl), OH, $OR^6$, $OCHF_2$, $COOR^6$, $NH_2$, $NHR^6$, $NR^6R^7$ (wherein $R^7$ has the same meaning as $R^6$), $CONH_2$, $CONHR^6$, $CONR^6R^7$, $COSR^6$, $SR^6$, $S(O)R^6$, $S(O)_2R^6$, $S(O)_2R^6$, $SO_3H$, $SO_3R^6$, $SO_2NH_2$, $SO_2NHR^6$, $SO_2NR^6R^7$, CN and phenyloxy;

the nitrogen-containing hetero ring portion represents a 1,4-dihydropyridine ring;

Z is a group of the formula II:

(II)

wherein each of $R^4$ and $R^5$ which may be the same or different is OH, $C_1$-$C_{12}$ linear or branched primary or secondary alkyloxy, $C_3$-$C_6$ linear or branched unsaturated alkyloxy, $C_3$-$C_6$ cycloalkyloxy, $C_1$-$C_6$ alkoxy substituted by $C_3$-$C_6$ cycloalkyl, $OAr^2$ (wherein $Ar^2$ is phenyl which may be substituted by halogen, $C_1$-$C_3$ alkyl or $C_1$-$C_3$ alkoxy), $OANR^6R^7$ (wherein A is $C_2$-$C_6$ alkylene, which may be substituted by $C_1$-$C_3$ alkyl or $Ar^2$), $OAN(CH_2Ar^2)R^6$, $OAOR^6$, OACN, $NH_2$, $NHR^6$, $NR^6R^7$, 1-piperidinyl or 1-pyrrolidinyl, or $R^4$ and $R_5$ together form OY (wherein Y is $C_2$-$C_4$ linear saturated or unsaturated alkylene which may substituted by $R^6$, $CO_2R^6$, $OR^6$, or A), NHYO, $R^6NYO$, NHYNH, $R^6NYNH$ or $R^6NYNR^7$;

$R^1$ is hydrogen, $R^6$, $ANR^6R^7$, $AN(CH_2CH_2)_2O$, $AOR^6$ or $CH_2phenyl$;

$R^2$ is $R^6$, $Ar^2$, $Ar^2CH=CH$, $Ar^2CH(OH)CH_2$, CHO, CN, $CH_2OH$, $CH_2OR^6$, $CH_2CH_2N(CH_2CH_2)_2NR^6$, $NH_2$, or $NHR^6$;

$R^3$ is hydrogen, $C_1$-$C_{12}$ linear or branched alkyl, $C_3$-$C_6$ linear or branched unsaturated alkyl, $C_3$-$C_6$ cycloalkyl, $C_1$-$C_6$ alkyl substituted by $C_3$-$C_6$ cycloalkyl, $AOR^6$, $AO(CH_2)_mAr^2$ (wherein m is an integer of from 0 to 3), $(CH_2)_mAr^2$, $ANH_2$, $ANHR^6$, $ANR^6R^7$, $ANR^6(CH_2)_mAr^2$, $AN\{(CH_2)_mAr^2\}\{(CH_2)_nAr^3\}$ (wherein n has the same meaning as m, and $Ar^3$ has the same meaning as $Ar^2$), the 1-benzyl-4-piperidinyl, 1-benzyl-2-piperidinyl, 2-pyridinylmethyl, 3-pyridinylmethyl, AQ (wherein Q is pyrrolidine or piperidine which may be substituted by $(CH_2)_mAr^2$), 4-$R^6$-1-piperazinyl, 4-$Ar^2$-1-piperazinyl, 4-$(Ar^2)_2$CH-1-piperazinyl or 4-$(Ar^2)_2$CH-1-(1,4-diazacycloheptyl);

or a pharmaceutically acceptable salt of the compound.

2. The method according to claim 1, wherein any one of the substitutents $R^1$, $R^2$, $R^3$, $R^4$, and $R^5$ in the compound of the formula I contains at least one basic nitrogen atom capable of forming a salt.

* * * * *

UNITED STATES PATENT AND TRADEMARK OFFICE
CERTIFICATE OF CORRECTION

PATENT NO. : 5,304,550
DATED : April 19, 1994
INVENTOR(S) : Shin-ichi AKIYAMA, et al.

It is certified that error appears in the above-indentified patent and that said Letters Patent is hereby corrected as shown below:

On the title page, Item [*] and Item [45], the Terminal Disclaimer information has been omitted and should read as follows:

--[*] Notice: The portion of the term of this patent subsequent to Jul. 14, 2009 has been disclaimed.--

[45] Date of Patent: --*Apr. 19, 1994--

Signed and Sealed this

Thirteenth Day of September, 1994

Attest:

BRUCE LEHMAN

*Attesting Officer*   *Commissioner of Patents and Trademarks*